United States Patent [19]

Mayer

[11] Patent Number: 4,505,858

[45] Date of Patent: Mar. 19, 1985

[54] PROCESS FOR PRODUCING 3,4,9,10-TETRATHIOPERYLENE AND 3,4,9,10-TETRASELENOPERYLENE

[75] Inventor: Carl W. Mayer, Riehen, Switzerland

[73] Assignee: Ciba-Geigy Corporation, Ardsley, N.Y.

[21] Appl. No.: 538,022

[22] Filed: Sep. 30, 1983

[30] Foreign Application Priority Data

Oct. 12, 1982 [CH] Switzerland ............... 5962/82

[51] Int. Cl.³ .................... C07D 9/00; C07D 333/00
[52] U.S. Cl. .................................. 260/239 R; 549/31
[58] Field of Search ............... 549/31; 260/239 R

[56] References Cited

FOREIGN PATENT DOCUMENTS 446528  2/1948  Canada ........................... 549/31

OTHER PUBLICATIONS

Journal of the American Society, (Jan. 7, 1976).
Journal of the American Society 99:1, 255, (1977).
Journal of Organic Chemistry, vol. 30, No. 12, Dec. 13, 1965.
Organometallics 1982, 1, 739–742.
Chem. Ber. 55, 330, (1922).
Scholl–Reaklieu Chem. Ber. 91, 2109, (1958).
Solid State Communications, vol. 38, No. 12, pp. 1129–1134.
E. Clar. Polycyclic Hydrocarbons, (1964), Dissertation, J. Veige, Universitat Heidelberg, Germany, (1981).

Primary Examiner—Alan Siegel
Attorney, Agent, or Firm—Michael W. Glynn

[57] ABSTRACT

Chalcogen-substituted perylenes of the formula I

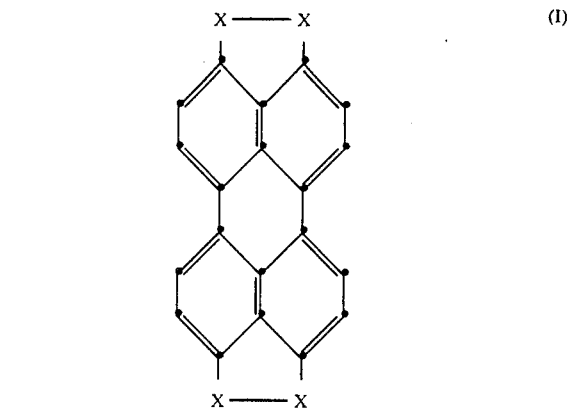

wherein X is S or Se can be obtained in a simple manner, under mild reaction conditions and in pure form by heating a compound of the formula II

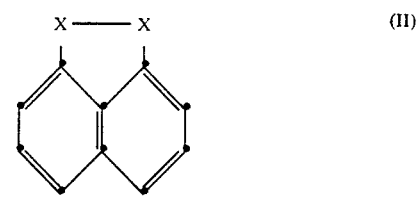

in nitrobenzene, or in a mixture of nitrobenzene and an organic solvent miscible therewith and inert under the reaction conditions, in the presence of a Lewis acid or a protonic acid at 20° to 120° C. The perylenes of the formula I are used for example as donors for the production of organic conductors or semiconductors (charge-transfer-salts).

7 Claims, No Drawings

PROCESS FOR PRODUCING 3,4,9,10-TETRATHIOPERYLENE AND 3,4,9,10-TETRASELENOPERYLENE

The present invention relates to a novel process for producing 3,4,9,10-tetrathioperylene and 3,4,9,10-tetraselenoperylene. It is known that polycyclic aromatic compounds which are modified in the peri-positions by chalcogen bridges are valuable donors for organic conductors or seiconductors: cp. for example German Patent Specification No. 2,641,742 and U.S. Pat. No. 3,984,593; J. Am. Chem. Soc., 98: 1, 252 (1976) and 99: 1, 255 (1977); J. Org. Chem., 30, 3997 (1965) and U.S. Pat. Nos. 3,403,165 and 3,634,366. In the last-named U.S. patent specification there are mentioned, among a great number of polycyclic aromatic compounds modified with chalcogen bridges, also tetrachalcogenperylenes, such as 3,4,9,10-tetrathio-3,4,9,10-tetratelluro- and 3,4,9,10-tetraselenoperylenes. According to the process known from Organometallics, 1, 739 (1982) for the production of 5,6,11,12-tetratellurotetracene by reaction of 5,6,11,12-tetrachlorotetracene with sodium ditelluride, in the presence of N,N-dimethylformamide or hexamethylphosphoramide, 3,4,9,10-tetrathio- 3,4,9,10-tetratelluro- or 3,4,9,10-tetraselenoperylene cannot be produced in pure form and/or only in traces. Also the reaction with sodium diselenide produces products which still contain chlorine (J. Veigl, Dissertation, University Heidelberg 1981).

Unsubstituted perylene or 1,12- and 3,10-dihydroxyperylene can be produced for example by the heating of naphthalene or naphthalene derivatives, such as 1-bromonaphthalene, 1,1'-binaphthyl, 1,1'- or 2,2'-binaphthol, in the presence of aluminium chloride, to about 150°–160° C. The yields are howver generally very low. Unsubstituted perylene can be obtained also by cyclisation of 1,1'-binaphthyl in the presence of at least 36% hydrofluoric acid and mangenese dioxide at about 140° C.; by the heating of 2,2'-binaphthol with phosphorus pentachloride and phosphoric acid to 400°–500° C., or with phosphorus oxychloride and zinc dust to 500°–600° C.; or by distillation of 1,12- or 3,10-dihydroxyperylene with zinc dust. In the case of these prior known processes, it is hence necessary to use really drastic reaction conditions, which various substituents on the naphthalenes or naphthalene derivatives, inter alia chalcogen bridges, do not withstand (cp. for example E. Clar, Polycyclic Hydrocarbons, Vol. 2, p. 24 ff., Academic Press (1964).

It is on the other hand known that, according to the Scholl reaction, 1,1'-dimethoxy- or 1,1'-diethoxy-4,4'-binaphthyl is formed by gently heating 1-methoxy- or 1-ethoxynaphthalene in the presence of nitrobenzene and a Lewis or protonic acid, especially aluminium chloride or benzenesulfonic acid. When for example 1,8-dimethoxynaphthalene is used in place of 1-methoxynaphthalene, there occurs under the stated reaction conditions likewise only a linkage to form 1,1',8,8'-tetramethoxy-4,4'-binaphthyl [cp. for example Ber. 55, 330 (1922) and Chem. Ber. 91, 2109 (1958)].

It has now been found that the chalcogen-substituted perylenes of the formula I

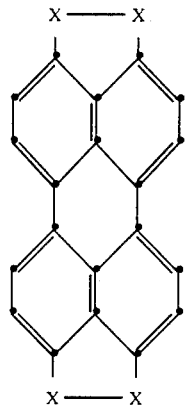

wherein X is S or Se, can surprisingly be produced in a simple manner, under mild conditions and in a pure form by heating a compound of the formula II

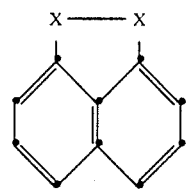

wherein X has the meaning defined under the formula I, in nitrobenzene, or in a mixture of nitrobenzene and an organic solvent miscible therewith and inert under the reaction conditions, in the presence of a Lewis acid or a protonic acid at 20° to 120° C.

For the reaction of the compound of the formula II wherein X is S, there is preferably used a Lewis acid and the reaction temperatures are advantageously between 20° and 40° C., whereas for the reaction of the compound of the formula II wherein X is Se, protonic acids and reaction temperatures of between 80° and 100° C. are preferred.

Suitable Lewis acids are for example: aluminium trichloride, aluminium tribromide, $BF_3$, tin tetrachloride, zinc chloride and titanium tetrachloride. The Lewis acid preferably used is aluminium trichloride.

Suitable protonic acids are for example: hydrohalic acids, such as HF, HCl and HBr, sulfuric acid, phosphoric acid, polyphosphoric acid or optionally halogenated aliphatic carboxylic acids, such as dichloroacetic acid and trifluoroacetic acid, particularly however aliphatic or aromatic sulfonic acids, such as methanesulfonic acid, benzenesulfonic acid, p-toluenesulfonic acid or naphthalenesulfonic acid. The protonic acid preferably used is an aromatic sulfonic acid, especially benzenesulfonic acid or p-toluenesulfonic acid.

As organic solvents inert under the reaction conditions and miscible with nitrobenzene, there can be used for example aromatic hydrocarbons, such as benzene or toluene. When mixtures of nitrobenzene and an inert solvent miscible therewith are used, the proportion of nitrobenzene per mol of the compound of the formula II is advantageously at least ½ mol. The reaction is preferably performed in pure nitrobenzene, particularly anhydrous nitrobenzene.

The processing of the compounds of the formula I is advantageously carried out in the presence of a reducing agent, such as TiCl₃, in order to bring any parts of the final product oxidised by the nitrobenzene into the desired form. The crude products obtained according to the invention are advantageously purified by sublimation.

The starting products of the formula II are known [cp. J. Am. Chem. Soc., 99: 1, 255 (1977)].

The compounds of the formula I are suitable—as already mentioned—for example as donors for the production of organic conductors or semiconductors, whereby as electron acceptors there can be used for example benzoquinones of the type mentioned in the U.S. Pat. No. 3,403,165, halogens, such as chlorine, bromine and especially iodine, $PF_6^-$, $AsF_6^-$, $SbF_6^-$, $TaF_6^-$, $ClO_4^-$, $ReO_4^-$ or $FSO_3^-$, 7,7,8,8-tetracyanoquinodimethane or organic acids, such as carboxylic acids or sulfonic acids (cp. for example U.S. Pat. No. 3,634,336). Conducting complexes formed from 3,4,9,10-tetrathioperylene and iodine can be produced for example by co-sublimation of 3,4,9,10-tetrathioperylene and iodine [cp. Solid State Comm., 38, 1129 (1981)].

EXAMPLE 1

6.9 g (51.74 mmols) of aluminium chloride are dissolved in 200 ml of anhydrous nitrobenzene under argon in a 350 ml sulfonating flask. The solution is cooled to 10° C. and a solution of 7.6 g (40 mmols) of naphtho-[1,8-c,d]-1,2-dithiole in 70 ml of anhydrous nitrobenzene is then added. The formed dark-blue mixture is subsequently stirred firstly for ½ hour at 10° C. and then for 24 hours at 40° C., in the course of which a red-violet suspension precipitates. The reaction mixture is afterwards poured into 500 ml of 1N HCl and thoroughly stirred. There are added 50 ml of 15% TiCl₃ in 10% HCl, and the mixture is stirred for 1 hour. After filtration under suction, the solid substance obtained is well washed with water and diethyl ether, and dried under high vacuum at 40° C./0.13 Pa. The yield is 2.2 g (29% of theory) of crude tetrathioperylene. The crude product is subsequently sublimed at 300° C./0.13 Pa, and the pure tetrathioperylene then precipitates as small golden, lustrous needles (1.2 g; about 16% of theory). Identification by means of mass spectrum: $M^+ = 376$; vis-spectrum in 1,2,4-trichlorobenzene: $\lambda_{max}$ 572 nm and 531 nm; crystal structure according to X-ray: monoclinic, space group P2₁/n (centrosymmetrical); axes: a=16.149 Å, b: 4.013 Å, c=22.292 Å, $\beta=94.54°$.

EXAMPLE 2

A mixture of 1.0 g (3.49 mmol) of naphthol[1,8-c,d]-1,2-diselenole and 5.0 g (31.6 mmol) of anhydrous benzenesulfonic acid in 100 ml of anhydrous nitrobenzene is stirred under argon in a 250 ml three-necked flask for 20 hours at 100° C. The red-violet solution is then concentrated under high vacuum. After drying overnight at 60° C. under high vacuum, there are added to the oily residue about 250 ml of 10% sodium bicarbonate solution. The crystalline precipitate then forming is filtered off under suction, repeatedly washed with sodium bicarbonate solution and subsequently with 1N HCl solution, and afterwards stirred up for 30 minutes with 15% TiCl₃ in 10% HCl (20 ml). The product is finally washed neutral with water and dried under high vacuum to thus obtain 1 g (100% of theory) of crude product. The crude product is sublimed at 375° C./0.13 Pa, as a result of which 110 mg (11% of theory) of pure tetraselenoperylene are obtained in the form of small silvery lustrous needles. Identification by means of mass spectrum: $M^+ = 564$, isotope cluster corresponds to 4 Se atoms per molecule; vis-spectrum in benzene: $\lambda_{max}$ 574 nm, 532 nm; crystal structure according to X-ray: monoclinic, space group P2₁/c; axes a=7.896 Å, b: 4.201 Å, c=22.578 Å, $\beta=90.57°$.

What is claimed is:

1. A process for producing chalcogen-substituted perylenes of the formula I

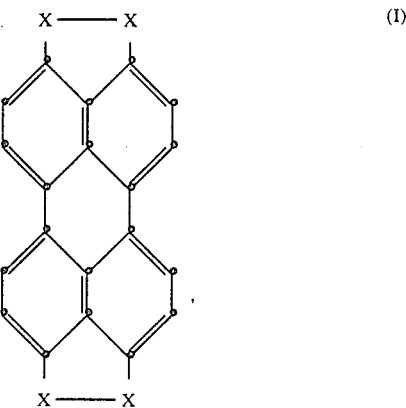

wherein X is S or Se, which process comprises heating a compound of the formula II

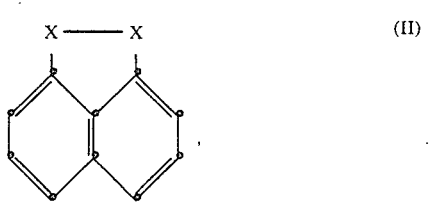

wherein X has the meaning defined under the formula I, in nitrobenzene, or in a mixture of nitrobenzene and an organic solvent miscible therewith and inert under the reaction conditions, in the presence of a Lewis acid or a protonic acid at 20° to 120° C.

2. A process according to claim 1, wherein the compound of the formula II wherein X is S is heated in the presence of a Lewis acid at 20° to 40° C.

3. A process according to claim 2, wherein the compound of the formula 2 wherein X is S is heated in the presence of aluminium chloride at 20° to 40° C.

4. A process according to claim 2, wherein the compound of the formula II wherein X is Se is heated in the presence of a protonic acid at 80° to 100° C.

5. A process according to claim 2, wherein the compound of the formula II wherein X is Se is heated in the presence of an aromatic sulfonic acid at 80° to 100° C.

6. A process according to claim 2, wherein the compound of the formula II wherein X is Se is heated in the presence of benzenesulfonic acid or p-toluenesulfonic acid at 80° to 100° C.

7. A process according to claim 1, wherein the reaction is performed in pure nitrobenzene, particularly in anhydrous nitrobenzene.

* * * * *